US011395892B2

(12) United States Patent
Judson et al.

(10) Patent No.: US 11,395,892 B2
(45) Date of Patent: Jul. 26, 2022

(54) CUSHION ASSEMBLY FOR A RESPIRATORY MASK

(71) Applicant: ResMed Pty Ltd, Bella Vista (AU)

(72) Inventors: Daniel Robert Judson, Lapstone (AU); Justin John Formica, Voyager Point (AU); Renee Frances Flower, Eastwood (AU); Donald Darkin, Dural (AU); Phillip Rodney Kwok, Chatswood (AU); Grant Moiler, Chipping Norton (AU); David Anthony Pidcock, Castle Hill (AU); Gregory Robert Peake, Petersham (AU); Aaron Samuel Davidson, Mona Vale (AU); Damien Julian Mazzone, Concord West (AU)

(73) Assignee: ResMed Pty Ltd

( * ) Notice: Subject to any disclaimer, the term of this patent is extended or adjusted under 35 U.S.C. 154(b) by 400 days.

(21) Appl. No.: 16/296,784

(22) Filed: Mar. 8, 2019

(65) Prior Publication Data
US 2019/0314593 A1  Oct. 17, 2019

Related U.S. Application Data

(63) Continuation of application No. 13/382,427, filed as application No. PCT/AU2010/000805 on Jun. 25, 2010, now Pat. No. 10,238,825.
(Continued)

(51) Int. Cl.
*A61M 16/06* (2006.01)
*A61M 16/00* (2006.01)

(52) U.S. Cl.
CPC ........ *A61M 16/06* (2013.01); *A61M 16/0622* (2014.02); *A61M 16/0057* (2013.01)

(58) Field of Classification Search
CPC .... A61M 16/06–0666; A61M 16/0057; A62B 25/005; A62B 18/082; A62B 18/02;
(Continued)

(56) References Cited

U.S. PATENT DOCUMENTS

| 4,513,741 A * | 4/1985 | Demi ...................... A61D 7/04 128/206.29 |
| 4,751,757 A | 6/1988 | Moreno |

(Continued)

FOREIGN PATENT DOCUMENTS

| WO | 2009062265 A1 | 5/2009 | |
| WO | WO-2009062265 A1 * | 5/2009 | ........ A61M 16/0622 |

OTHER PUBLICATIONS

International Search Report PCT/AU2010/000805 dated Aug. 2, 2010.

*Primary Examiner* — Elliot S Ruddie
(74) *Attorney, Agent, or Firm* — Botos Churchill IP Law LLP

(57) ABSTRACT

A mask cushion or a mask assembly therewith provides a comfortable and effective seal for provision of a gas therapy by a respiratory treatment apparatus. The mask cushion may be integrated with or coupled to a mask frame. The mask cushion typically includes an inner cushion component. The mask cushion also includes a patient facial-contact side portion with a chamber and a barrier to form the chamber that may be flexible. The chamber may serve as an outer layer with respect to the inner cushion component. The chamber may be partially or completely filled with a gas, fluid or gel. The inner cushion may be formed with a soft flexible material such as an elastomer or foam, etc. The barrier may be a membrane and may also be soft flexible material.

19 Claims, 18 Drawing Sheets

Related U.S. Application Data

(60) Provisional application No. 61/223,503, filed on Jul. 7, 2009.

(58) Field of Classification Search
CPC . A62B 18/084; B64D 10/00; B64D 2231/025
USPC ............ 128/200.24, 202.27, 205.25, 206.24,
128/206.26, 206.28, 206.21, 206.23,
128/207.11, 857, 858, 863
See application file for complete search history.

(56) References Cited

U.S. PATENT DOCUMENTS

| | | | |
|---|---|---|---|
| 4,811,730 A * | 3/1989 | Milano | ............. A61M 16/0048 128/202.28 |
| 4,936,298 A * | 6/1990 | Nishina | ................. A61M 16/06 128/205.13 |
| 6,112,746 A | 9/2000 | Kwok | |
| 6,357,441 B1 | 3/2002 | Kwok | |
| 6,513,526 B2 | 2/2003 | Kwok | |
| 6,581,602 B2 | 6/2003 | Kwok | |
| 6,634,358 B2 | 10/2003 | Kwok | |
| 6,701,927 B2 | 3/2004 | Kwok | |
| 6,871,649 B2 | 3/2005 | Kwok | |
| 7,069,933 B2 | 7/2006 | Kwok | |
| 7,178,527 B2 | 2/2007 | Kwok | |
| 7,243,651 B2 | 7/2007 | Kwok | |
| 2007/0006882 A1 | 1/2007 | Chang | |
| 2007/0107733 A1 | 5/2007 | Ho et al. | |
| 2007/0163594 A1* | 7/2007 | Ho | .................... A61M 16/0616 128/206.24 |
| 2008/0149104 A1 | 6/2008 | Eifler | |
| 2008/0289633 A1 | 11/2008 | Kwok | |
| 2011/0088699 A1* | 4/2011 | Skipper | ................. A61M 16/06 128/206.26 |

* cited by examiner

CUSHION ASSEMBLY FOR A RESPIRATORY MASK

CROSS-REFERENCE TO RELATED APPLICATIONS

This application is a continuation of U.S. patent application Ser. No. 13/382,427 filed on Feb. 3, 2012 which is a national phase entry under 35 U.S.C. § 371 of International Application No. PCT/AU2010/000805, filed Jun. 25, 2010, published in English, which claims priority from U.S. Provisional Patent Application No. 61/223,503 filed Jul. 7, 2009, all of which are incorporated herein by reference.

FIELD OF THE TECHNOLOGY

The present technology relates to masks used in therapeutic applications. More particularly, it relates to cushions of masks that may be used with respiratory treatment apparatus.

BACKGROUND OF THE TECHNOLOGY

Typically a respiratory treatment apparatus can provide a patient with a supply of breathable gas (usually air, with or without supplemental oxygen) at a therapeutic pressure or pressures, at appropriate times during the subject's breathing cycle. Such therapies may include continuous positive airway pressure (CPAP), nasal intermittent positive pressure ventilation (NIPPV) and variable positive airway pressure (VPAP), for example. The therapy may be used for treatment of various respiratory conditions including sleep disordered breathing (SDB) and more particularly obstructive sleep apnea (OSA). These apparatus typically require a mask or other patient contact device to direct the delivery of the treatment gas to the respiratory system (e.g., a patient's nares, mouth or both). If such a device is configured to deliver pressures above atmospheric pressure, it may be desirable for a mask to have a design that is both comfortable for the wearer but that can provide an effective seal against mask leaks.

BRIEF SUMMARY OF THE TECHNOLOGY

In an aspect of the present technology, a cushion for a respiratory mask provides a comfortable and effective seal for delivering breathable gas to a patient's airways to permit the patient to receive treatment with a respiratory treatment apparatus.

In another aspect of the present technology, a cushion for a respiratory mask provides an interface for contacting the face of a patient. The cushion may include an inner cushion component. The cushion may further include a patient contact side portion such that the patient contact side portion includes at least a chamber that may optionally be flexible and a barrier or wall, that may optionally be a membrane, to form the chamber. The chamber may serve as an outer layer with respect to the inner cushion component. This cushion may optionally be coupled to a mask frame that includes a port for coupling with a gas supply system, such as a tube.

In some embodiments, the chamber includes a gas or a fluid therein. The gas may optionally be air. The fluid may optionally be (but not restricted to) water, saline solution, oil or a liquid gel.

In still further embodiments of the technology, the cushion may include a top facial-contact portion, an inner side wall portion adjacent to the top facial-contact portion and an outer side wall portion adjacent to the top facial-contact portion. In such an embodiment, the barrier and chamber are formed to extend along a limit of the top facial-contact portion. In some further embodiments, the barrier or barrier membrane and chamber are formed to extend along a limit of the top facial-contact portion and inner side wall portion. In still others, the barrier or barrier membrane and chamber are formed to extend along a limit of the inner side wall portion, the top facial-contact portion and the outer side wall portion. Optionally, the barrier or barrier membrane and chamber are formed to extend along and around a perimeter of the inner cushion component.

Some embodiments of the mask cushion may also employ an inner barrier or inner barrier membrane to separate the inner cushion component from the fluid.

Optionally, the inner cushion may be or include a soft foam, balls or pellets or a three-dimensional spacer fabric. Still further, the inner cushion component may comprise a porous structure formed of an elastomeric material.

In some embodiments, the barrier(s) or barrier membrane(s) may be formed of an elastic material. The mask cushion may also include a mask frame interconnect coupled with at least one of, some or all of the inner cushion component(s) and the barrier(s) or barrier membrane(s). Optionally, the mask frame interconnect may serve as a cap integrally formed with the inner cushion component. The cap may serve to seal the inner cushion and/or the chamber and may also reduce a number of parts of the mask cushion or assembly.

In some embodiments, the patient contact side portion of the mask cushion is shaped to conform to the face of a patient so as to seal or surround a patient's nose or nares. In some embodiments, the patient contact side portion is shaped to conform to the face of a patient so as to also seal or surround the patient's mouth.

Further embodiments and features of the technology may be apparent from the following detailed disclosure and the drawings.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

Figure 1:
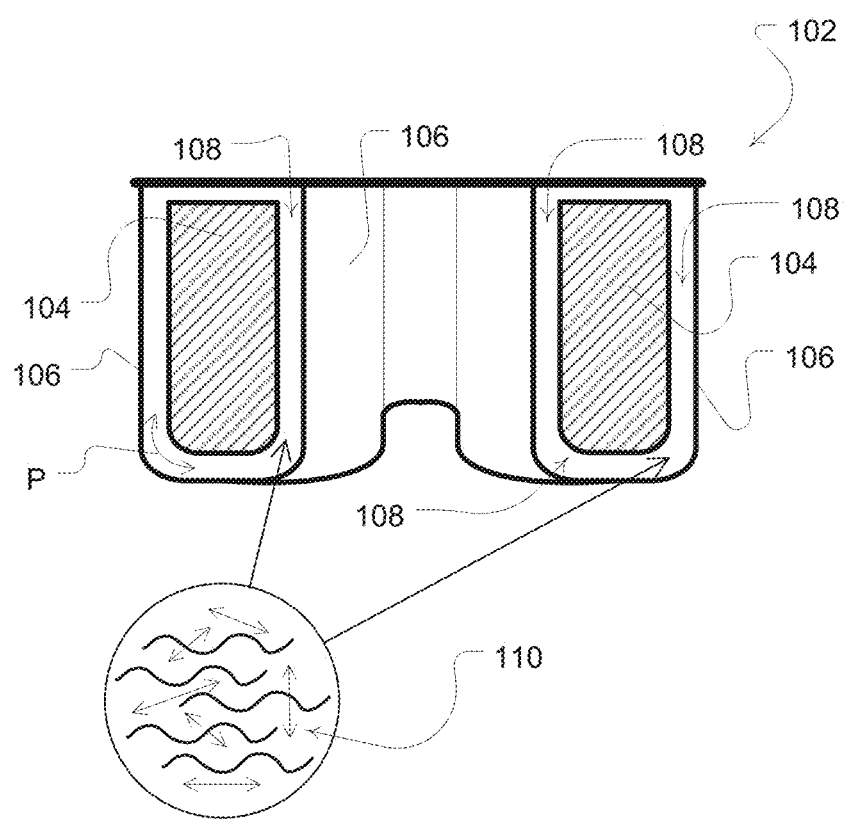
FIG. 1 shows a cross-sectional view of an embodiment of a mask cushion of the present technology taken along line 2-2 of the mask cushion embodiment of FIG. 2.

Embodiments of the present mask cushion technology may be implemented to provide a patient mask with a comfortable fit and effective seal for treatment with a respiratory treatment apparatus. In a typical embodiment, a mask cushion 102 may employ an inner cushion component 104. An outer barrier 106, which may optionally be a membrane, that may be applied to the inner cushion to form a chamber 108 or cell with respect to the inner cushion component 104. The chamber may optionally be flexible. The outer barrier 106 and chamber can serve as a patient contact side of the mask cushion 102 relative to the inner cushion component. Thus, in some embodiments the inner nature of the cushion component may be more distal with respect to a mask-to-face point-of-contact with the patient when compared with the more proximal outer nature of the barrier or barrier membrane that may be at least in partial contact with a facial feature of a patient. Moreover, the inner cushion component may be wholly or partially encapsulated by the outer barrier. In such a case, the chamber may be a cavity formed by an outer barrier and inner cushion component.

Typically, the inner cushion component may be soft and/or elastic and the outer barrier may be a pliable and/or elastic layer of natural or synthetic material. However, in some embodiments it may be formed at least in part with a rigid or semi-rigid material. Optionally, the inner cushion component may serve as at least a partial filler of the outer barrier.

In some embodiments, each barrier or membrane may be formed from silicone, polyurethane and/or polyethylene. The barrier may even be formed of a viscoelastic material. A pliable and/or elastic nature of either or both of the components and/or membranes of the mask cushion may serve to provide the chamber with a flexible property. In some embodiments, the barrier may be thin, such as on the order of the range of about 0.2 to 5 millimeters. Preferably, the barrier may be about 0.2 to 0.6 millimeters. However, in some embodiments it may even exceed this range and may also be sufficiently pliable to permit sealing with the particular areas or contours of the patient's face to permit a comfortable and effective seal while also maintaining the inner substance of the chamber.

Moreover, the outer barrier can serve to retain a chamber material 110 within the chamber, such as a gas or liquid, between the inner cushion and the outer barrier or outer barrier membrane or within an area substantially confined by the barrier. The chamber material may fill or only partially fill the chamber depending on the desired response characteristics of the mask cushion. Preferably, the chamber material may move, flow, permeate within the chamber or otherwise deform in response to applied patient contact pressure on the flexible or elastic components of the cushion such as the outer barrier or outer barrier membrane. For example, an outer layer of liquid may reside and flow within the chamber formed between the outer barrier and the inner cushion component. Thus, in some embodiments, the structure and flexibility provided by the inner cushion component can enable a mask utilizing such a cushion component to conform with a patient's macro facial features (e.g., nose and/or mouth) while the outer layer of the chamber may accommodate for micro facial topography. Similarly, depending on the chosen viscosity or deformability of the chamber material of the chamber, the outer barrier may respond more rapidly than the inner cushion with respect to changes in facial contour resulting from movement during use (e.g., facial expressions) so as to maintain a more effective seal against respiratory treatment leaks.

Figure 2:
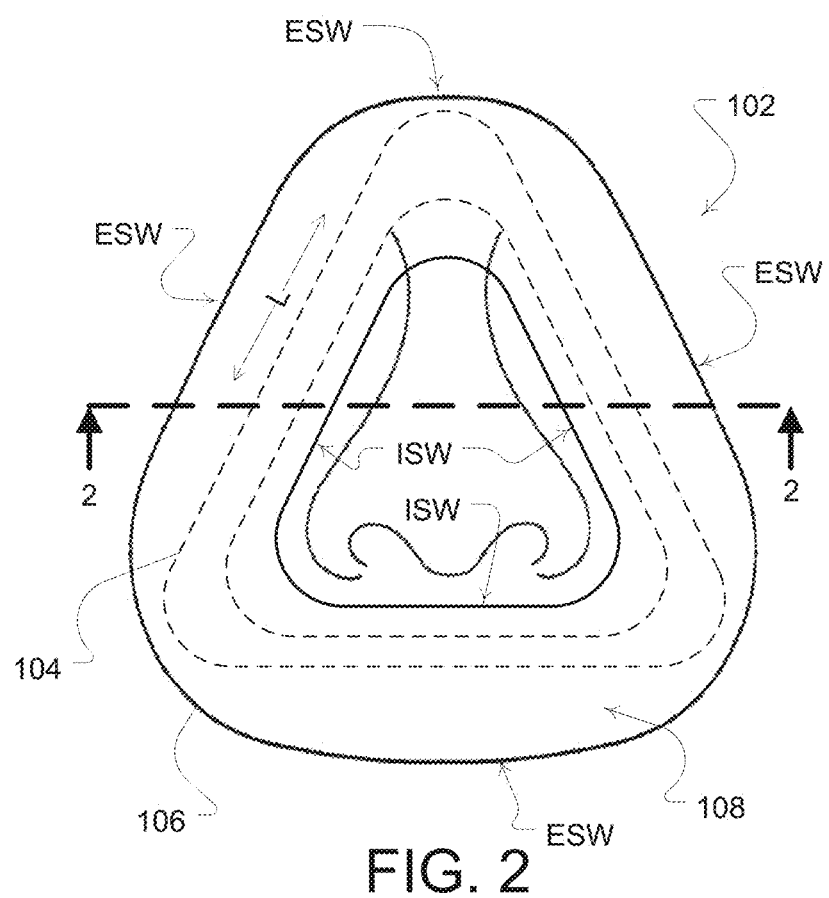
FIG. 2 shows an example embodiment of a mask cushion for a nasal mask.

As illustrated in the embodiment of FIGS. 1 and 2, the outer barrier 106 may form a chamber that may surround a perimeter of the inner cushion component 104 (shown as line P) in addition to extending along a length (shown as line L) of the inner cushion component. However, the chamber and inner cushion may be formed in various configurations. The chamber may be formed by one or a plurality of discrete cells that each contain the same chamber material or different chamber materials depending on the desired flexibility to be achieved by the different sections or cells of the chamber. Additional example embodiments showing various chamber configurations are illustrated in the cross-sectional illustrations of FIGS. 3 through 6.

Figure 3:
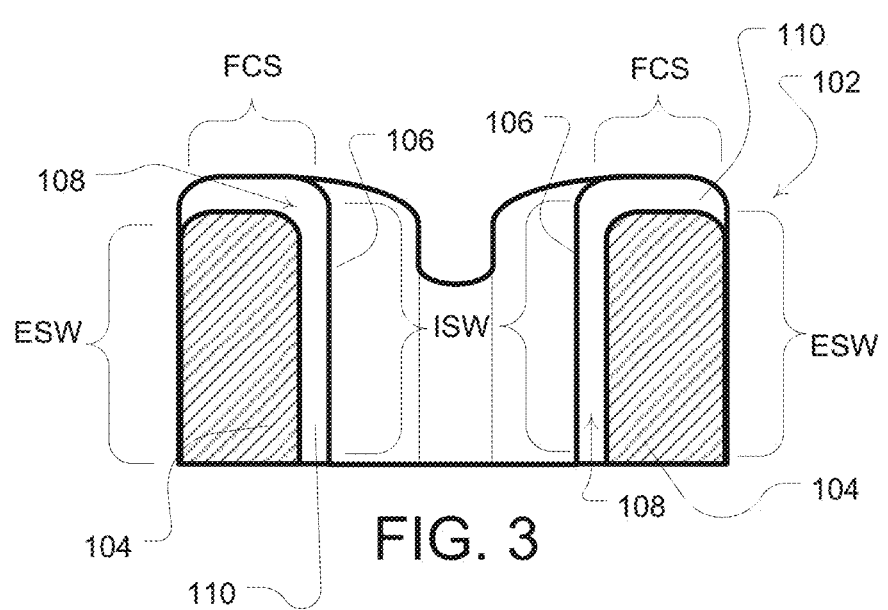
FIG. 3 is a cross-sectional view of another embodiment of a removable mask cushion for a mask frame with a partial chamber.
Figure 4:
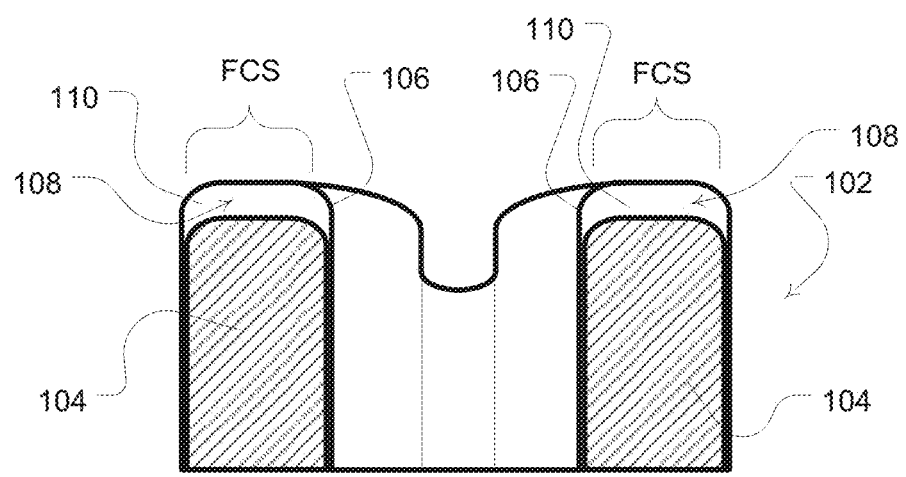
FIG. 4 illustrates a cross-sectional view of another embodiment of a removable mask cushion for a mask frame with another partial chamber.
Figure 5:
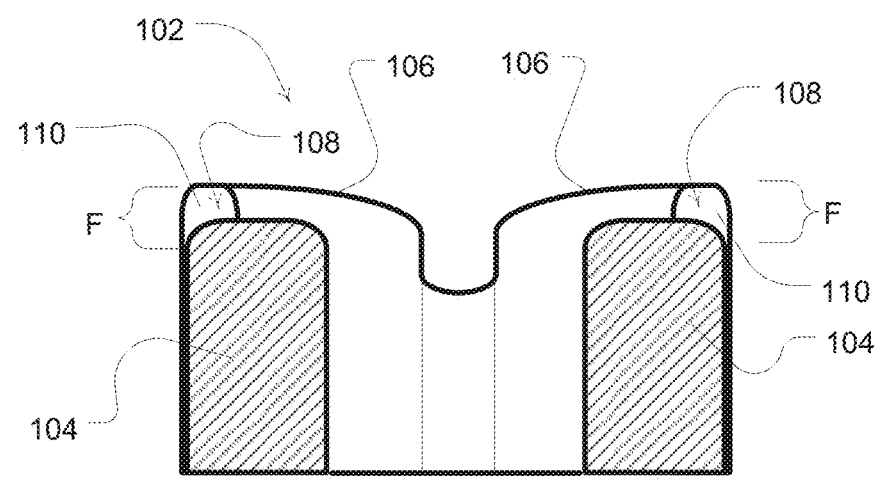
FIG. 5 illustrates a cross-sectional view of a still further embodiment of a removable mask cushion for a mask frame with another partial chamber.

In FIG. 3, a chamber extends along a partial perimeter of the inner cushion component. In this example, a chamber substantially extends along a limit of an Interior Side Wall portion (shown as "ISW" in FIG. 3 and FIG. 1) of the mask cushion and along a limit of a Face Contact top Side portion (shown as "FCS") but not substantially along the Exterior Side Wall portion (shown as "ESW" in FIG. 3 and FIG. 1). In FIG. 4, the chamber extends substantially along a limit of the face contact top side portion of the mask cushion without extending substantially along either of the interior side wall portions or the exterior side wall portions. In the example of FIG. 5, the chamber is formed along a limit of a portion of the facial-contact top side portion of the mask cushion to form a chamber flap F that may be flexible. Although the flap F portion of FIG. 5 is illustrated extending from the facial-contact top side portion near an exterior side wall portion, an alternative or additional flap portion (not shown) may optionally extend from the facial-contact top side portion near the interior side wall portion. Optionally, although each of these embodiments is generally shown as a substantially continuous enclosed chamber, the interior side wall portion, exterior side wall portion and the facial-contact top side portion in some embodiments may each be formed by a discrete cell of the chamber and may be adjacent to one or more of the other discrete cells of the chamber.

Figure 6:
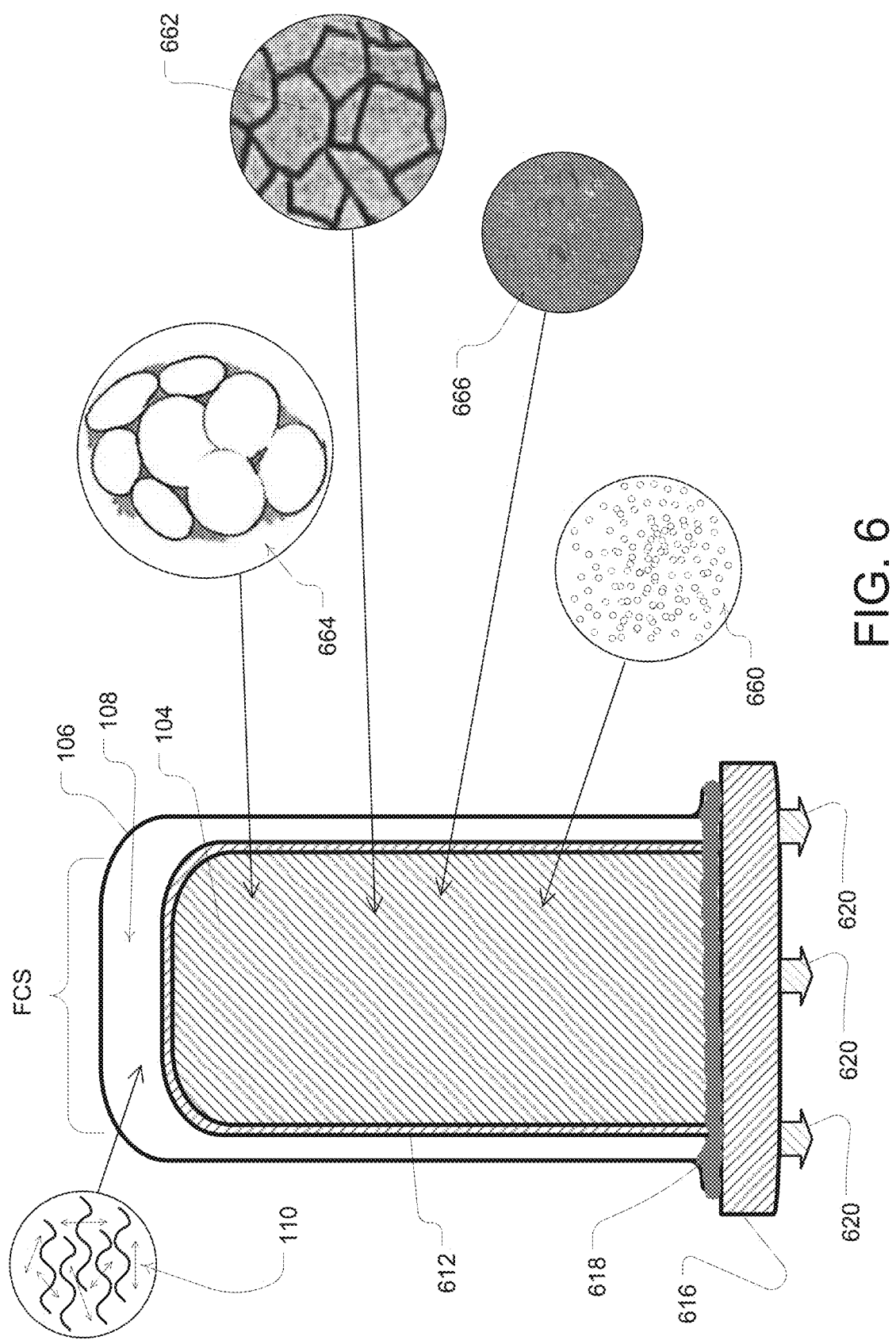
FIG. 6 is a cross-sectional view of a still further embodiment of a portion or part of the mask cushion of the present technology illustrating various filler materials.

Beneficially, the different materials or material properties of the components of the cushion may be combined to yield a synergistic performance when used as a cushion for a respiratory mask. Thus, as illustrated in FIG. 6, the inner cushion component of any of the embodiments may be a soft springing foam 660 such as an open cell or closed cell foam. This component may optionally be formed with a polyether, urethane or other elastomer 662. It may also be formed with a gel 666 or such a gel with air bubbles, beads, pellets and/or foam balls 664 therein. In such a case, the beads, pellets and/or foam balls may be soft and/or flexible. Alternatively, the beads, pellets, or the like may not be soft. For example, they may be semi-rigid or rigid. Preferably, the beads, pellets, or the like may be flowable through the liquid in which they are suspended. Optionally, such beads, pellets and/or foam balls may be in a liquid or any other of the inner cushion component or chamber materials. The inner cushion component may even be formed with an open cell foam that is saturated or impregnated by a gel. By way of further example, the inner cushion component may be formed with three dimensional spacer fabrics such as in a matrix structure or other three dimensional structure or pattern and is saturated or impregnated by a gel.

When the chamber material is a flowable substance or other material having a sufficiently low viscosity to promote its movement throughout the chamber, one or more benefits discussed herein may be achieved. For example, the material may be a gas such as air or a liquid such as water, a liquid gel, saline solution or oil. The material may also be sterile. With such a low viscosity, the chamber material 110 may not only move through the chamber, but it may also optionally flow so as to permeate through or within the material or structure of the inner cushion component. Thus, in some embodiments, the chamber material may saturate the inner cushion component or move through a porous or open structure of the inner cushion component to the extent that the portion of the inner cushion component is encapsulated or retained within the enclosure of the chamber. Such a permeation of the fluid within, for example, a foam inner cushion component can provide an inner cushion with a density greater than without the fluid and it can then provide a different feeling for a patient upon contact or under pressure.

Figure 17:
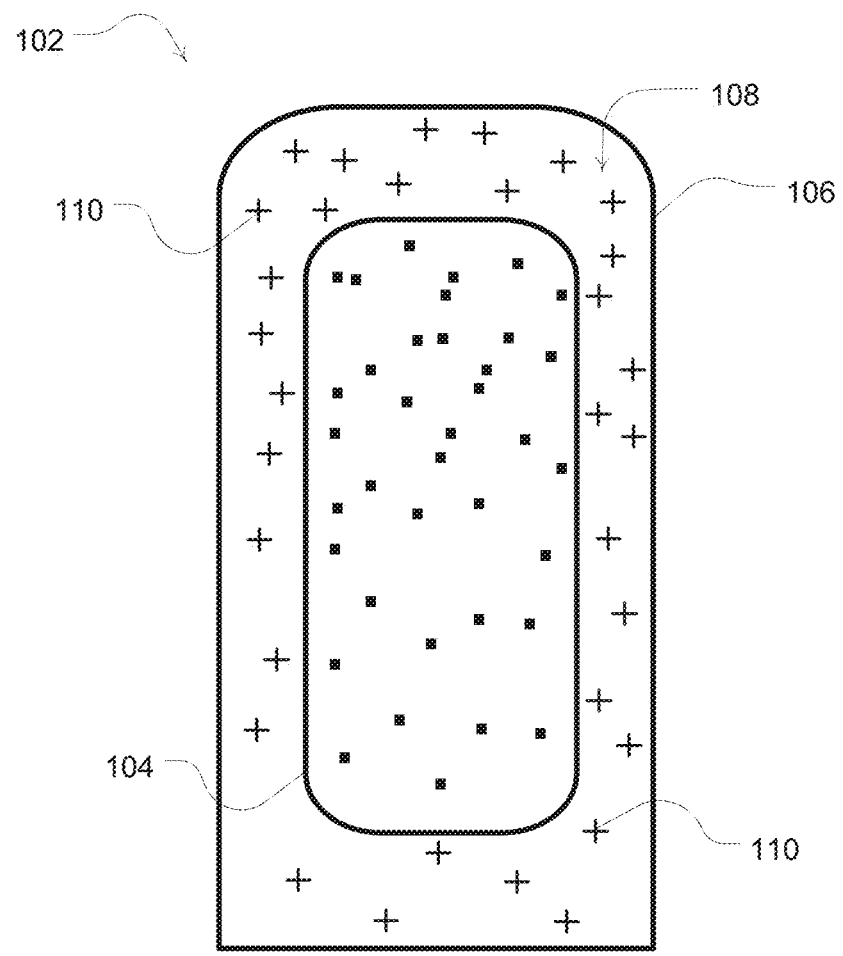
FIG. 17 is an illustration of a cross section of an example mask cushion in a non-compressed state.
Figure 18:
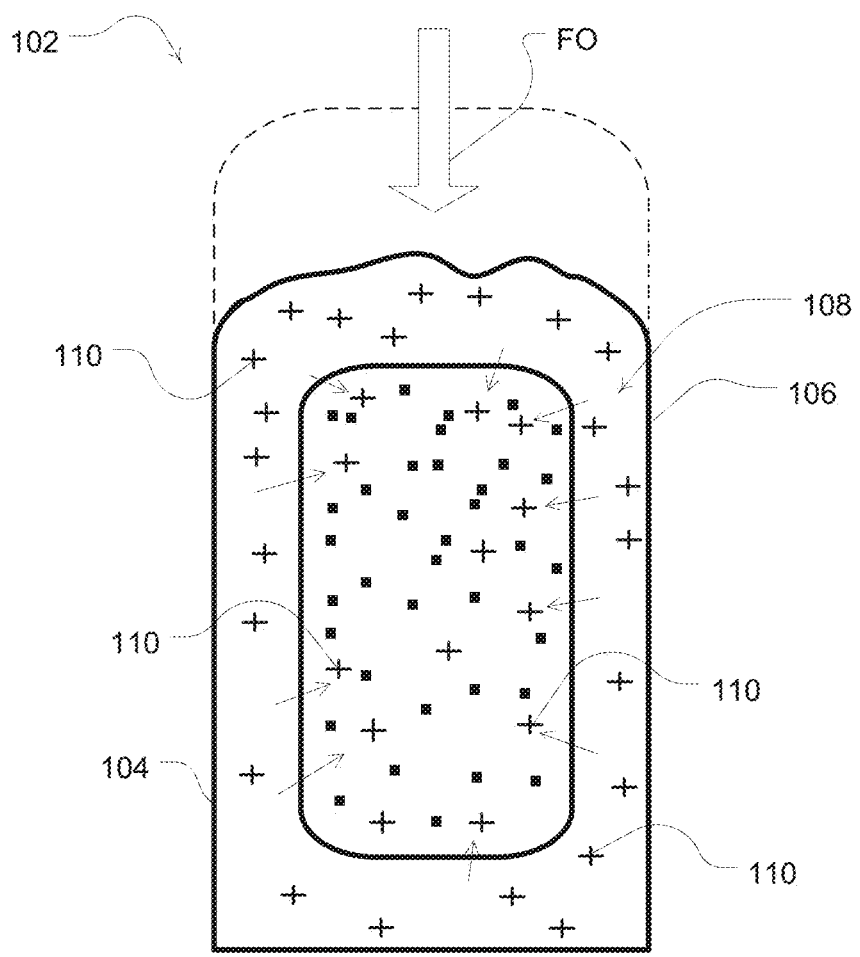
FIG. 18 is an illustration of a cross section of the example mask cushion of FIG. 17 in a compressed state due to force FO.

An example of a migration of the chamber material, such as a fluid or gas, between the chamber and the inner cushion component may be considered with reference to FIGS. 17 and 18. In this example, the mask cushion 102 has the chamber material 110, represented by "+" symbols in these figures, within the chamber 108. When an external force FO, such as a patient contact on the outer barrier 106 as illustrated in FIG. 18, is applied, chamber material 110 may flow (illustrated by the arrows of FIG. 18) as the mask cushion is compressed. Thus, under a load, the outer chamber material may migrate to the inner cushion component, or an aperture thereof, at a rate that is viscoelastic in nature. Releasing the load or force FO may then permit the mask cushion 102 to return to its non-compressed state illustrated by FIG. 17. In such a case, the chamber material 110 may return to the chamber 108 as the force FO recedes.

However, in some embodiments, such as the cushion illustrated in FIG. 6, an optional internal barrier membrane 612 may be included to impede or prevent the chamber material from permeating through or within the material or structure of the inner cushion component. In this way, the internal barrier membrane may internally encapsulate the inner cushion component and prevent material aggregation between the two. Thus, inner and outer barrier membranes can serve as a dual seal bladder for the chamber material. For example, gels of different viscosities could be utilized for the inner cushion component and chamber material. For example, a gel with a higher viscosity may be utilized for the material of the inner cushion component (within the inner barrier membrane) and a lower viscosity gel could be utilized for the chamber material in the chamber. Similarly, the flow of a fluid such as water in the chamber can be prevented from combining with, for example, a gel inner cushion component with the inner barrier membrane therebetween. By way of further example, by preventing a permeation of the fluid such as water within, for example, a foam inner cushion component, the inner cushion may be provided with a lighter feel for patient use. Furthermore, by varying the ratio of a quantity of foam for the inner cushion component with a quantity of liquid in the chamber, the hardness or comfort of the mask cushion as perceived by the patient may be adjusted. Similarly, by otherwise varying the degrees of the flexibility or pliability of the inner cushion component with respect to the flexibility or pliability of the chamber and/or outer barrier can provide unique mask performance qualities.

As further illustrated in FIG. 6, the components of the mask cushion of the present technology may include an integrated or separate mask interconnect component 616, which may optionally be adhered with an adhesive 618 or other fastening compound or component. The mask interconnect component can serve as an attachment device to combine the cushion with a mask frame for a mask assembly. In this example, the mask interconnect component 616 includes optional clips 620 for temporarily affixing the interconnect to the mask frame. The mask interconnect component 616 can also serve as a cap to assist with retaining the chamber material within the outer barrier membrane. Thus, the interconnect may be adhered with the outer barrier membrane as illustrated in the example of FIG. 6. It may also optionally be adhered to the inner cushion component and inner barrier membrane, if implemented in such an embodiment.

Figure 7:
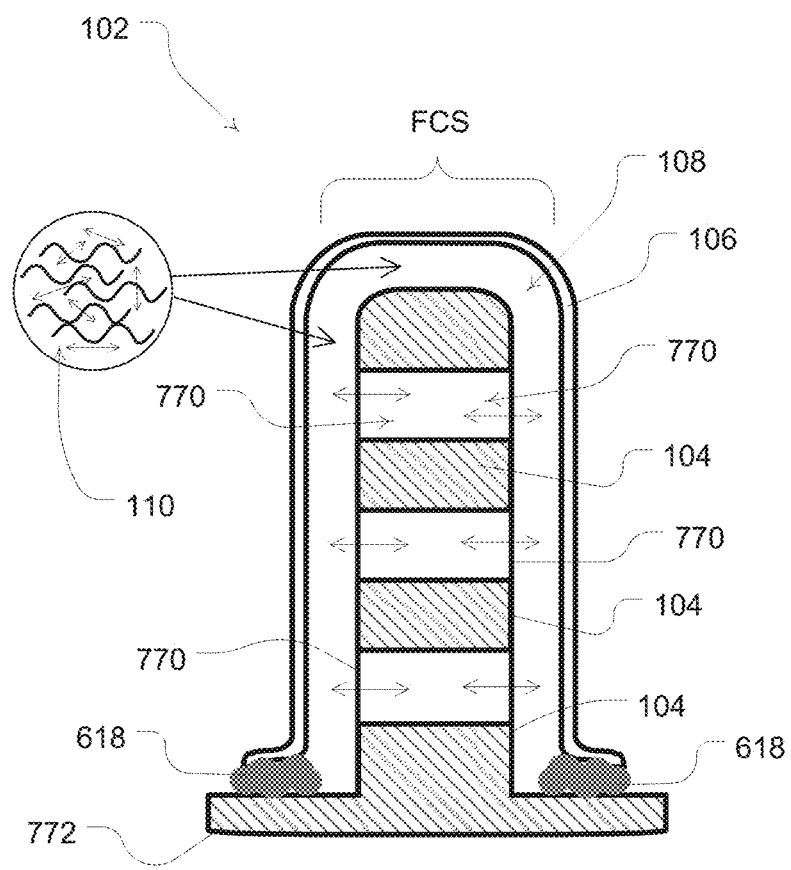
FIG. 7 is an still further cross-sectional view of part of an embodiment of a mask cushion of the present technology employing a porous inner cushion structure.
Figure 8:
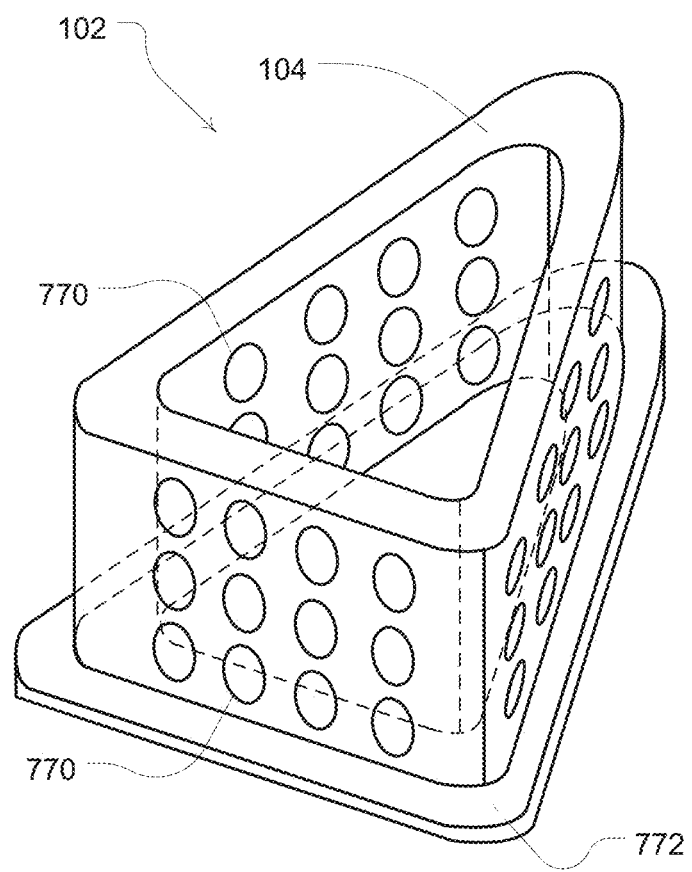
FIG. 8 is an illustration of the structure of the porous inner cushion component of the part of the mask cushion of FIG. 7.

A further example embodiment of a mask cushion of the present technology is illustrated in FIG. 7 with the inner cushion component 104 illustrated in FIG. 8. The mask cushion 102 in this embodiment may similarly include features of the previously discussed embodiments. In this embodiment, the chamber material 110 is permitted to flow into and through pores or structural apertures 770 molded into the structure of the inner cushion component. Such apertures may optionally be round, oval, rectangular, triangular or other shape. Thus, when pressure is applied to the outer barrier membrane a chamber material 110 of the chamber may flow through one or more structural apertures 770 of the inner cushion component. In this embodiment, the outer barrier membrane is adhered to a cap portion 772, which may optionally serve as an interconnect component or may be integral with a portion of a mask frame. In the illustrated version of FIGS. 7 and 8, the cap portion 772 is formed integrally with the inner cushion component 104.

Figure 9:
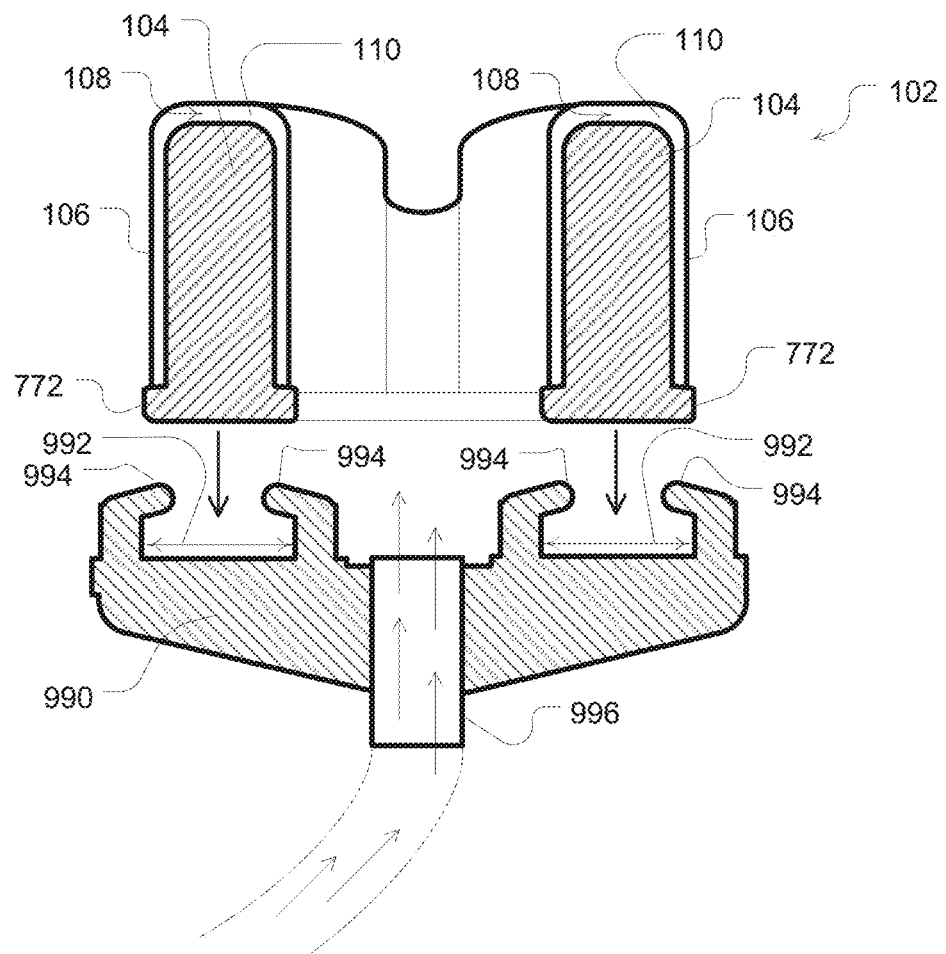
FIG. 9 illustrates another embodiment of a removable mask cushion and an example mask frame with a channel for retaining the mask cushion.
Figure 10:
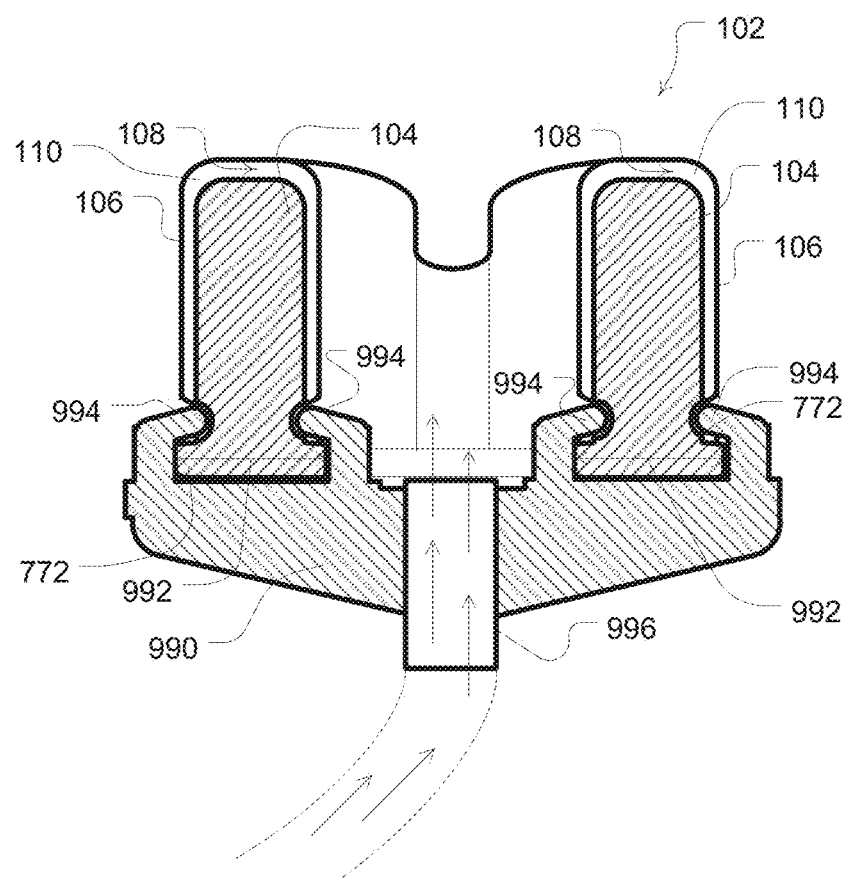
FIG. 10 is an illustration of the embodiment of a mask cushion of FIG. 9, assembled into the retention channel of the mask frame.

A further implementation of a removable mask cushion 102 for a mask frame 990 is illustrated in the embodiment of FIGS. 9 and 10. In this version, the flexible nature of the material used for the cap portion 772 of the inner cushion component 104, permits the cap portion 772 of the inner cushion component to serve as an interconnect to a mask frame. In the example, the mask frame includes a channel 992 sized for fitting with the cap portion. As shown in FIG.

10, the mask cushion may then be push fit or otherwise inserted into and retained by the channel 992. The compression fitting formed by ridges 994 of the channel 992 and the flexibility of the cap portion 772, outer barrier membrane and/or inner cushion component create a pressure seal to prevent a treatment gas pressure leak between the mask frame and mask cushion when gas is supplied to the mask via a gas port 996 of the mask frame.

Figure 11:
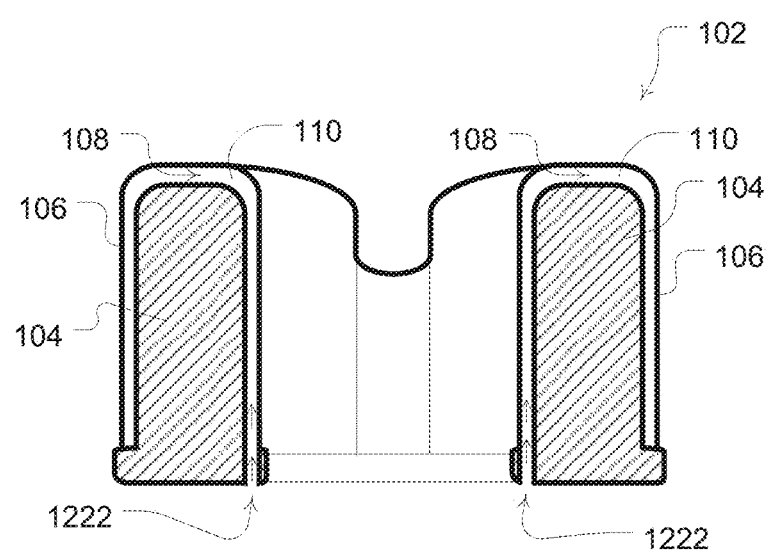
FIG. 11 is a cross-sectional view of a further mask cushion embodiment of the present technology including a chamber supply orifice.

In some embodiments, the substance that is within the chamber 108 may be inserted in a bladder formed by the barrier membrane prior to (or after) the insertion of the inner cushion component and prior to the affixing of the cap portion to the barrier membrane. However, in some embodiments, the mask cushion may include a perforation or chamber supply orifice 1222 such as the example illustrated in FIG. 11. In the embodiment of FIG. 11, the orifice 1222 may be utilized to insert the substance within the chamber and then may be suitably capped to enclose it. For example, a cap portion may be inserted in the chamber supply orifice in the case of the use of a liquid, for example, to prevent its escape during use.

Figure 12:
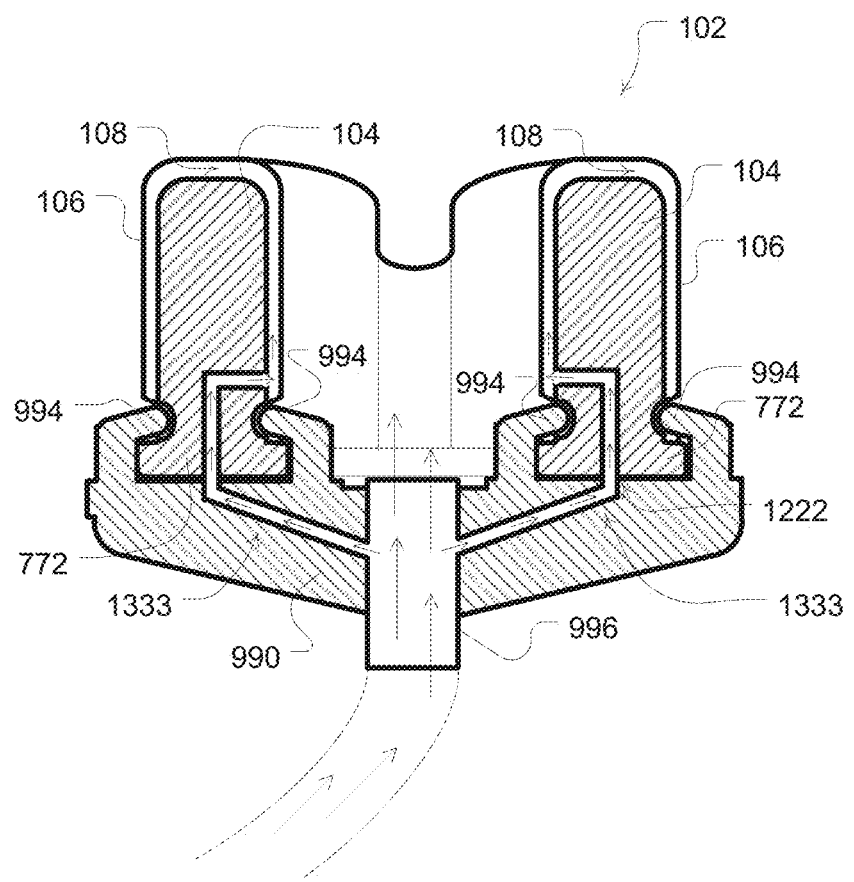
FIG. 12 is a cross-sectional view of an example mask cushion embodiment illustrating a supply orifice coupling with an chamber supply duct of a mask frame.

However, in some embodiments, the chamber supply orifice to the chamber may remain open even during use, which may then permit a more dynamic supply of a substance to the chamber. For example, in the illustrated embodiment of FIG. 12, a chamber supply duct 1333, such as a tube, may be coupled with one or more chamber supply orifici when the cushion is coupled with a mask frame 990. The duct, which may optionally be formed with the mask frame, may then supply a gas (e.g., treatment air) to the chamber during operation of a flow generator of the respiratory treatment apparatus to which the mask is coupled. In the example, the treatment gas (shown as arrows in FIG. 12) may supply the inner mouth (and/or nose) portion of the mask through the gas port 996. The treatment gas may also traverse the chamber supply duct 1333 and its coupling to the chamber supply orifice(s) 1222 to pressurize the chamber. In this embodiment the chamber supply orifice(s) 1222 is through the inner cushion component 104 and the cap portion 772. However, in other embodiments the orifice may be formed with or by the barrier membrane 106 rather than the inner cushion component.

Figure 13:
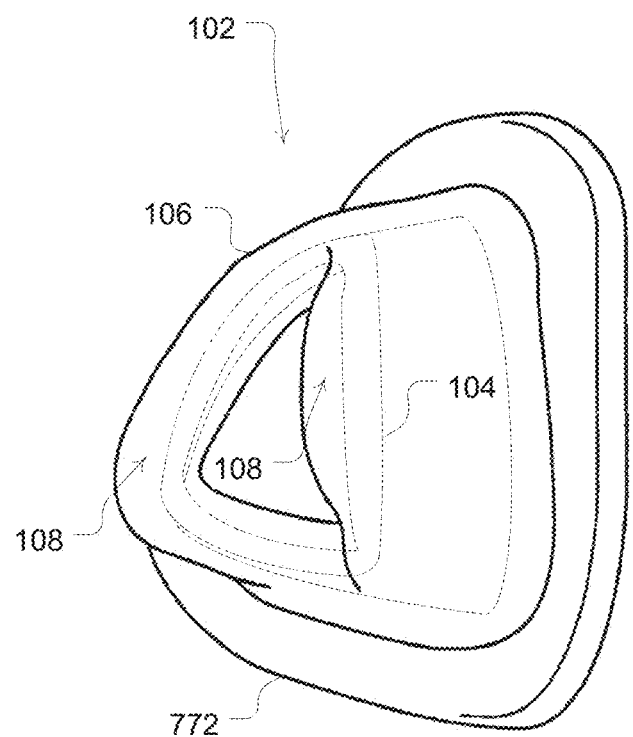
FIG. 13 is an illustration of an embodiment of a nasal mask cushion of the present technology.
Figure 14:
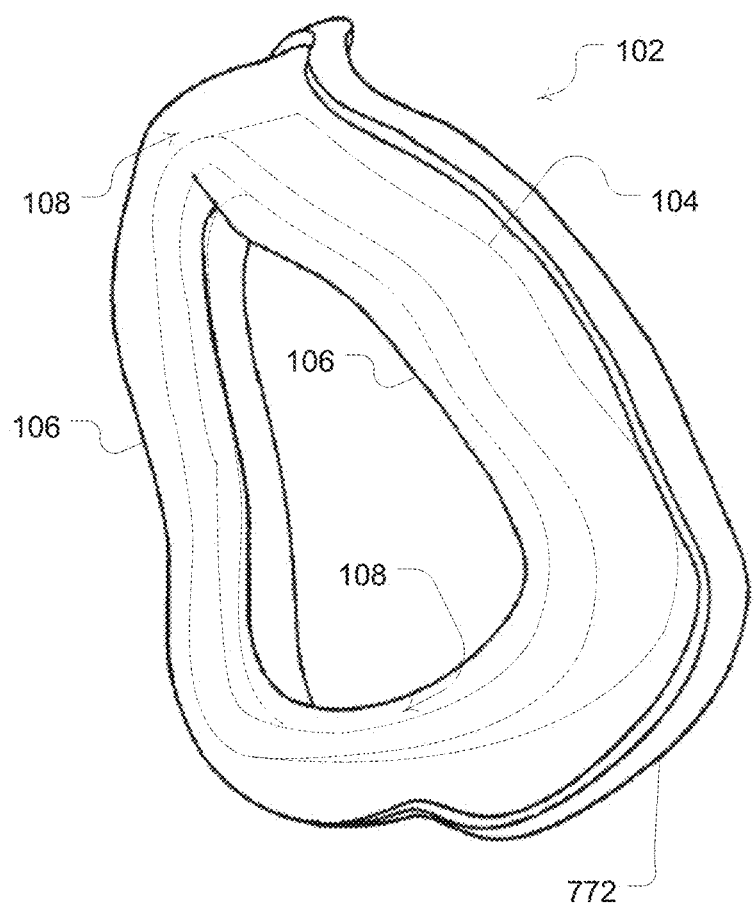
FIG. 14 is an illustration of an embodiment of a nose and mouth mask cushion of the present technology.
Figure 15:
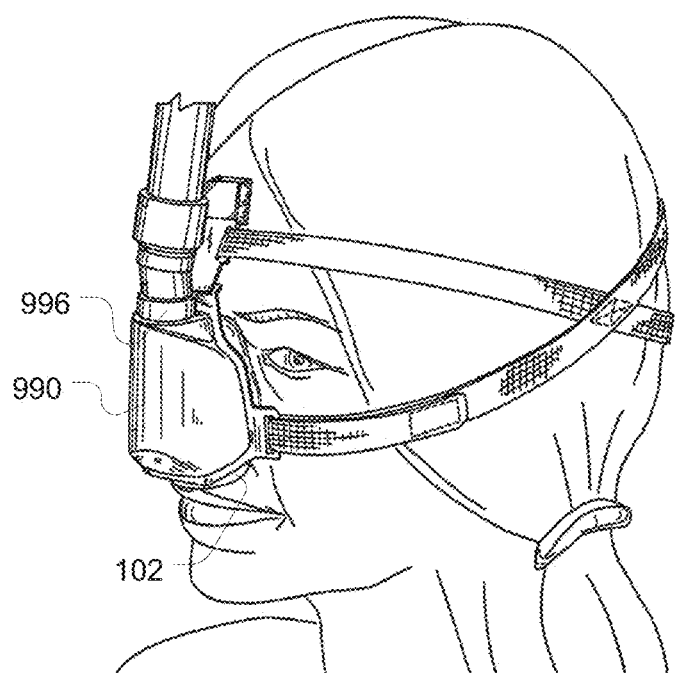
FIG. 15 is an illustration of a patient employing the mask cushion of FIG. 13.
Figure 16:
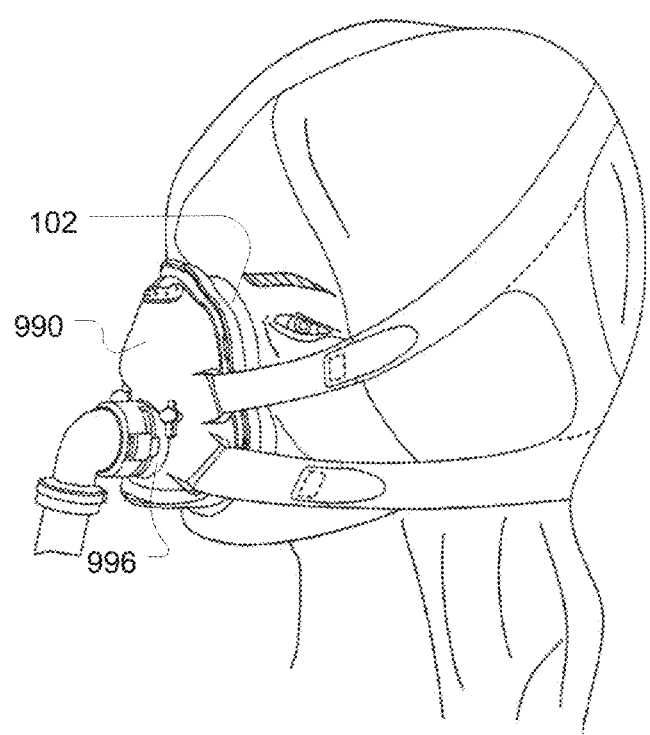
FIG. 16 is an illustration of a patient employing the mask cushion of FIG. 14.

The features of the present mask cushion technology as described herein may be applied to many different mask types and shapes. For example, as illustrated in FIGS. 13 and 14 respectively, the technology may be applied to a nasal mask cushion or a nose and mouth mask cushion. Thus, when applied to suitable frames as illustrated in FIGS. 15 and 16 respectively, the cushions may serve as part of either a nasal mask assembly or a nose and mouth mask assembly, etc. The present invention may also be applied to pillows masks.

In the foregoing description and in the accompanying drawings, specific terminology and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, in addition to the chamber features described herein, the embodiments of the mask may further include an open flap seal of the type disclosed in U.S. Pat. Nos. 6,112,746, 6,357,441, 6,513,526, 6,634,358, 6,871,649, 6,581,602, 7,178,527, 6,701,927, 7,069,933 and 7,243,651, the disclosures of which are incorporated herein by reference.

The invention claimed is:

1. A mask assembly for a respiratory treatment apparatus comprising:
    a mask frame, the mask frame including a port for coupling with a gas supply tube configured for pneumatic coupling with a flow generator, the gas supply tube for providing treatment air of a respiratory therapy, via the mask assembly, to a patient's respiratory system, the mask frame including ridges that define a channel; and
    a cushion coupled with the mask frame, the cushion comprising an inner cushion component and a patient contact side portion, the patient contact portion comprising a chamber and a barrier to form the chamber, the chamber comprising an outer layer with respect to the inner cushion component, the cushion comprising a mask interconnect component for removably engaging the channel to secure the cushion to the mask frame;
    wherein the mask interconnect component comprises a chamber supply orifice pneumatically coupled to the chamber,
    and wherein the mask frame further comprises a chamber supply duct coupled for gas flow to the chamber supply orifice, the chamber supply duct being pneumatically coupled to the gas supply tube to receive the treatment air and to convey the treatment air to the chamber supply orifice.

2. The mask assembly of claim 1 wherein the barrier comprises a membrane.

3. The mask assembly of claim 2 wherein the cushion comprises a top facial-contact portion, an inner side wall portion adjacent to the top facial-contact portion and an outer side wall portion adjacent to the top facial-contact portion, and wherein the barrier membrane and chamber are formed to extend along a limit of the top facial-contact portion.

4. The mask assembly of claim 2 wherein the cushion comprises a top facial-contact portion, an inner side wall portion adjacent to the top facial-contact portion and an outer side wall portion adjacent to the top facial-contact portion, and wherein the barrier membrane and chamber are formed to extend along a limit of the top facial-contact portion and inner side wall portion.

5. The mask assembly of claim 2 wherein the cushion comprises a top facial-contact portion, an inner side wall portion adjacent to the top facial-contact portion and an outer side wall portion adjacent to the top facial-contact portion, and wherein the barrier membrane and chamber are formed to extend along a limit of the inner side wall portion, the top facial-contact portion and the outer side wall portion.

6. The mask assembly of claim 2 wherein the barrier membrane and chamber are formed to extend along and around a perimeter of the inner cushion component.

7. The mask assembly of claim 2 wherein the barrier membrane comprises an elastic material.

8. The mask assembly of claim 1 wherein the chamber is a flexible chamber.

9. The mask assembly of claim 1 wherein the chamber includes a gas therein.

10. The mask assembly of claim 1 further comprising an inner barrier membrane to separate the inner cushion component from the treatment air of the chamber.

11. The mask assembly of claim 1 wherein the inner cushion comprises a soft foam.

12. The mask assembly of claim 1 wherein the inner cushion comprises balls or pellets.

13. The mask assembly of claim 1 wherein the inner cushion comprises a three-dimensional spacer fabric.

14. The mask assembly of claim 1 wherein the inner cushion component comprises a porous structure formed of an elastomeric material.

15. The mask assembly of claim 1 wherein the patient contact side portion is shaped to conform to the face of the patient to seal with the patient's nose.

16. The mask assembly of claim 15 wherein the patient contact side portion is shaped to conform to the face of the patient to seal with the patient's mouth.

17. The mask assembly of claim 1 wherein the chamber supply orifice and the chamber supply duct in the mask frame are configured so that, in use, the chamber supply orifice is coupled to the chamber supply duct at a connection of the chamber supply duct and the chamber supply orifice.

18. The mask assembly of claim 1 wherein the inner cushion component comprises a flow channel configured to supply the received treatment air from the duct to the chamber that comprises the outer layer.

19. The mask assembly of claim 1, wherein the mask interconnect component defines a duct therein pneumatically coupled to the chamber supply orifice to receive the treatment air and to convey the treatment air to the chamber.

\* \* \* \* \*